(12) United States Patent
Srinivas et al.

(10) Patent No.: US 6,521,789 B1
(45) Date of Patent: Feb. 18, 2003

(54) PROCESS FOR THE PREPARATION OF ADIPIC ACID

(75) Inventors: Darbha Srinivas, Pune (IN); Suhas Arunkumar Chavan, Pune (IN); Paul Ratnasamy, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 9 days.

(21) Appl. No.: 10/032,382

(22) Filed: Dec. 21, 2001

(51) Int. Cl.[7] .................. C07C 51/245; C07C 51/31
(52) U.S. Cl. ............... 562/528; 562/538; 562/542; 562/543; 562/546
(58) Field of Search .................... 562/528, 538, 562/542, 543, 546

(56) References Cited

U.S. PATENT DOCUMENTS

| 3,390,174 | A | * | 6/1968 | Schultz et al. |
| 4,263,453 | A | * | 4/1981 | Schultz et al. |
| 6,147,256 | A | * | 11/2000 | Constantini et al. |

* cited by examiner

*Primary Examiner*—Sreeni Padmanabhan
*Assistant Examiner*—Sikarl A. Witherspoon

(57) ABSTRACT

The present invention relates to an improved process for the preparation of adipic acid. More particularly, the present invention relates to an environmental-friendly, clean process for the preparation of adipic acid through oxidation of cyclohexanol, cyclohexanone or a mixture thereof with oxygen or oxygen-containing gas, in the presence of an oxidation initiator, a polar solvent and an organometallic $\mu_3$-oxo-bridged Co/Mn cluster complex catalyst.

17 Claims, No Drawings

PROCESS FOR THE PREPARATION OF ADIPIC ACID

FIELD OF THE INVENTION

The present invention relates to an improved process for the preparation of adipic acid. More particularly, the present invention relates to an environmental-friendly, clean process for the preparation of adipic acid through oxidation of cyclohexanol, cyclohexanone or a mixture thereof with oxygen or oxygen-containing gas, in the presence of an oxidation initiator, a polar solvent and an organometallic $\mu_3$-oxo-bridged Co/Mn cluster complex catalyst.

BACKGROUND OF THE INVENTION

Adipic acid is a large volume commodity chemical and is used in the manufacture of synthetic fibers (e.g, Nylon-6,6), polyurethane resins. plasticisers, food additives, lubricants, electronics, soil conditioners, glass protection agents and leather tanning agents. More than two million tons of adipic acid is produced worldwide per year, mostly, by a two-step oxidation process (Du Pont U.S. Pat. Nos. 2,233,494 (1940); 2,439,513 (1948); 2,825,742 (1958); 3,035,092 (1962); 3,390,174; BASF British Pat. Nos. 852,523 (1958); 918,900 (1963); British Pat. 1,304,855) wherein cyclohexane, in the first-step, is oxidized with oxygen, at 423–433 K, using a cobalt catalyst to form a cyclohexanone and cyclohexanol mixture (KA oil). In the second step the mixture is further oxidized to adipic acid with nitric acid, in the presence of V and Cu-containing catalysts. Conversion levels of cyclohexane, in the first step, are to be maintained below 10% to achieve acceptable selectivity of cyclohexanol-cyclohexanone. The second-step of the reaction (nitric acid oxidation) produces significant toxic nitrogen oxide effluents, and hence, is not environmental-friendly. The oxidation of cyclohexane is one of the least efficient of all the major industrial processes. Methods of improving the selectivity have been the focus of research in this area over the decades. Asahi Chelmical Industry (Japan Pat. No. 45-16,444 (1970)) and Gulf (U.S. Pat. No. 4,263,453 (1979)) have developed a direct single-step oxidation process of cyclohexane to adipic acid. In this process cyclohexane is oxidized with air or oxygen, in acetic acid medium and cobalt salt as catalyst, at reaction temperature of 343–373 K and residence time of 2–6 h. Cyclohexane conversion of the order of 50–94% and adipic acid selectivity of 70–80% have been reported in the single step process. Alternative single-step synthetic routes have been reported by Talsi et al (J. Mol. Catal. 81, 215 (1993)) and Maschmeyer et al (Angew. Chem. Int. Ed. Engl. 36, 1639 (1997)). However, the results on single-step oxidation to adipic acid have been less than satisfactory.

Kulsrestha et al in U.S. Pat. No. 5,547,905 (1996) have reported the preparation of adipic acid using Co and Fe containing homogeneous catalysts. U.S. Pat. No. 6,147,256 (2000) reports oxidation of cyclohexane in liquid phase using Co and Cr containing salts. Sato et al (Science 281, 1646 (1998)) have reported a process for the synthesis of adipic acid by oxidation of cyclohexene with $H_2O_2$ and solid $NaWO_4$ catalyst.

Kamath and Chandalia (J. Appl. Chem. Biotechnol. 23, 469–478 (1973)) have reported the preparation of adipic acid by the oxidation of cyclohexanone with air (atmospheric pressure), in the presence of acetic acid and cobalt acetate or manganese acetate salt, at 323–373 K. But the cyclohexanone conversion and adipic acid selectivities were very low, S. H. A. Zaidi (Appl. Catal. 42, 247 (1988)), E. T. Crisp and G. H. Whittfield (Great Britain Patent 2,818,807 (1978)) and T. N. Antonova, G. N. Koshel, and M. I. Farberov (Uch. Zap. Yaroslav, Tekhnol. Inst. 27, 100 (1971), CA 78(11): 71339p) have also reported the oxidation of cyclohexanone to adipic acid, but with lower conversions and adipic acid yields.

Raja and Ratnasamy in U.S. Pat. No. 5,767,320 (1998) have reported dioxygen oxidation of cyclohexane using pure and zeolite-Y-encapsulated substitute phthalocyanine catalysts; cyclohexanone and cyclohexanol were the selective products of the oxidation reaction Thomas et al have recently reported the preparation of adipic acid by aerial oxidation of cyclohexane or n-hexane using metal containing aluminophosphate molecular sieve catalysts (Nature 398, 227–230 (1999); Angew. Chem. Int. Ed. 39(13), 2310–2313 (2000); Angew. Chem. Int. Ed. 39(13), 2313 (2000)). U.S. Pat. Nos. 2,223,493; 2,589,648; 3,390,174; 3,649,689; 3,987,100; 4,263,453; 4,158,739; 4,902,827; 5,321,157 (1994); 5,981,420 (1999), 6,160.183 (2000). 6,258,981(2001) and EP-A-0,694,333 also describe other methods for the preparation of adipic acid. Comprehensive reports on the state-of the-art of adipic acid preparation are available in the reviews by K. Tanaka in CHEMTECH 555–559 (1974) and Hydrocarbon Process 53(11), 114–120 (1974), Castellan et al in Catal. Today 9(3), 237–322 (1991), Schuchardt et al in SYNLETT 713–718 (1993) and Appl. Catal. A. General 211, 1–17 (2001); Partenheimer in Catal. Today 23, 69–158 (1995); Suresh et al in Ind. Eng. Chem. Res. 39, 3958–97 (2000). However, in these reports adipic acid yields are lower than the commercial process and limit their applicability.

The commercial adipic acid manufacturing process has the following disadvantages: (1) the commercial process is not an environmentally benign or "green" approach. (2) nitrous oxide is an inevitable by-product, which has been implicated in global warming and ozone depletion, (3) substantial amount of nitric acid is consumed in the process, (4) decarboxylation to lower mono- and dicarboxylic acids is inevitable, and (4) 0.25 kg of by-products is produced per kg of the product, The present invention is an environmental-friendly green process. It does not use nitric acid, but utilizes cleaner oxidants like air or oxygen-containing gas. The method of the present invention utilizes an organometallic $\mu_3$-oxo-bridged Co/Mn cluster complex or a solid catalyst containing the organometallic $\mu_3$-oxo-bridged Co/Mn cluster complex as catalyst in a polar solvent medium like acetic acid-water in the presence of an oxidation initiator. Examples of such solid catalysts include micro and mesoporous materials like, aluminosilicate zeolites, aluminophosphates, carbon molecular sieves, silica and the like, containing an organometallic cluster complex wherein the chemical composition of each molecule of the organometallic cluster complex includes cobalt/manganese.

It is a surprising discovery of the present invention that when an organometallic $\mu_{l3}$-oxo-bridged Co/Mn cluster complex or the solid catalyst containing $\mu_3$-oxo-bridged cluster complex was used as catalyst the activity and adipic acid selectivity were significantly higher. In the experiments with the solid catalysts containing the organometallic cluster complex, the solid catalyst can be easily separated from the reaction mixture by filtration. Moreover the reaction conditions like temperature and pressure were moderate and the process was atom-efficient. The synergistic effect of a cobalt and manganese combination, and facile redox behavior in cluster complexes are perhaps responsible for high yields of adipic acid in the present invention.

Charvan et al in J. Mol. Catal. A. Chemical 161, 4964 (2000) and Chem. Commun. 1124–1125 (2001) teach that solid, encapsulated oxo-bridged metal cluster complexes are efficient catalysts in the aerial oxidation of para-xylene to terephthalic acid, an yet another large volume commodity chemical used in polyester industry. These novel solid catalysts while retaining all the advantages of the homogeneous catalysts, like high yield of adipic acid, are easily separable from the reaction products by a simple filtration process. This not only avoids the tedious process of catalyst recovery characteristic of the prior art processes, but also eliminates the presence of toxic metal ions and nitrous oxide in the effluents from the process. Processes utilizing these novel solid catalysts are, hence, environmentally more beneficial. Representatives of the organometallic cluster complexes of cobalt and manganese of the present invention are $Co_3(O)(CH_3COO)_6(py)_3$, $Mn_3(O)(CH_3COO)_6(py)_3$, $CoMn_2(O)(CH_3COO)_6(Py)_3$, $Co_2Mn(O)(CH_3COO)_6(py)_3$, $CoMn_2(O)(CH_3COO)_y(py)_z$, and $Co_2Mn(O)(CH_3COO)_y(py)_z$, where y+z=9 and py=pyridine. It is also found that the organic ligands in the above mentioned organometallic cluster complex, namely the acetate and pyridine ligands, can be replaced by other suitable organic moieties. The critical active site ensemble responsible for the high yields of adipic acids in the oxidation reaction was the heterometallic cluster complex containing both cobalt and manganese. While the exact origin of this enhancement effect is not known in detail, it may be speculated that the multimetallic clusters of transition metal ions are better able to activate oxygen, than the monometallic and monomeric ions. The common prevalence of such heteronuclear, multimetallic clusters in the oxygen activating enzymatic oxygenase catalyst systems supports such a suggestion.

OBJECTS OF THE INVENTION

The major object of the present invention is to provide an improved process for the preparation of adipic acid which an environmental-friendly and atom-efficient.

Another objective of the present invention is provide a process for the production of adipic acid wherein nitric acid is not used as an oxidant; cleaner oxidants like oxygen or oxygen-containing gas and a oxo-bridged Co/Mn cluster complex either in its neat form or contained in a solid matrix are used as catalyst.

Yet another objective of the present invention is to prepare adipic acid from cyclohexanol, cyclohexanone or a mixture thereof.

SUMMARY OF THE INVENTION

Accordingly, the present invention provides an improved process for the preparation of adipic acid which comprises oxidizing a cyclic compound selected from the group consisting of cyclohexanol, cyclohexanone and a mixture thereof in a polar solvent with oxygen in the presence of an $\mu_3$-oxo-bridged Co/Mn cluster complex catalyst and an oxidation initiator, at a pressure of at least 130 psig, at a temperature ranging between 353 and 403 K, for a period ranging from 0.5 to 8.0 hrs, bringing the temperature of reaction mixture to an ambient temperature and recovering the adipic acid from the reaction mixture by conventional methods.

In an embodiment of the present invention the cluster complex has a general formula

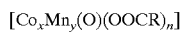
[$Co_xMn_y(O)(OOCR)_n$]

wherein x and y can take values of 0, 1, 2 or 3 and x+y=3, R is selected from the group consisting of alkyl, substituted alkyl group containing I or more carbon atoms, awl and substituted aryl group and n is in the range of 4 to 6.

In yet another embodiment the $\mu_3$-oxo cluster complex used is contained in a solid matrix selected from the group consisting of aluminosilicate zeolite, aluminophosphates, carbon molecular sieves and silica.

In yet another embodiment the polar solvent used is a mixture of alkyl or aryl carboxylic acid and water.

In yet another embodiment the oxygen used is selected from the group consisting of pure oxygen, air and a mixture of inert gases and oxygen.

In still another embodiment wherein the oxidation initiator used is selected from the group consisting of methyl ethyl ketone (MEK), acetaldehyde, hydrogen peroxide, alkyl hydroperoxide and halide ion preferably bromide ion.

This invention is illustrated by the following examples, which are illustrative only, and should not be construed to limit the scope of the present invention.

Preparation of Organometallic $\mu_3$-oxo-bridged Cluster Complexes

The said cluster catalyst has been prepared by a procedure as described and claimed in our co-pending U.S. patent application Ser. No. 09/894997.

EXAMPLE 1

This example illustrates the preparation of cobalt-manganese cluster catalyst $CoMn_2(O)(CH_3COO)_6$ (pyridine)$_3$ (hereafter designated as $CoMn_2(O)$). In a typical synthesis, 2.7 g of manganic acetate was taken in a solution containing 25 ml of absolute alcohol and 4.2 ml of glacial acetic acid. The mixture was stirred for 10 min till all the manganic acetate dissolved. To this 2.5 g of cobalt acetate tetrahydrate dissolved in 4 g of hot pyridine was added while stirring continuously. The solution was allowed to stand at 298 K from which shiny black crystals of $CoMn_2(O)$ were obtained.

EXAMPLE 2

This example illustrates the preparation of manganese cluster complex catalyst $Mn_3(O)(CH_3COO)_6$(pyridine)$_3$ (hereafter designated as $Mn_3(O)$). Manganese acetate tetrahydrate (2.5 g) was dissolved in a solvent mixture comprising of ethanol (20 ml), glacial acetic acid (12 ml) and pyridine (3 ml). The resulting solution was stirred while adding N-n-$Bu_4MnO_4$ (1.14 g) dissolved in 10 ml ethanol, in small proportions, over a period of 45 min, The resultant brown solution was stirred for 30 min. Then, 0.695 g of $NaClO_4$ was added and the stirring was continued for further 15 min. A brown crystalline product of $Mn_3(O)$ was obtained overnight on slow evaporation at 295 K. This was filtered, washed with ethanol and dried in vacuum.

EXAMPLE 3

This example illustrates the preparation of organometallic cobalt cluster catalyst $Co_3(O)(CH_3COO)_6$(pyridine)$_3$ (hereafter designated as $Co_3(O)$). Cobalt acetate tetrahydrate (1.25 g) was taken in a solution comprising of 12.5 ml of glacial acetic acid and 0.4 ml of pyridine and warmed at 323 K while stirring until all the solid was dissolved. The purple colored solution was then cooled to 298 K and a freshly prepared peracetic acid (obtained from the addition of 0.4 g of glacial acetic acid and 0.7 g of 30% $H_2O_2$) was added drop-wise over a period of 30 min while stirring. During the addition of peracetic acid the color of the solution changed to dark brown. Then, 3 ml of water was added and refluxed for 1 h at 353 K. A solution of $NaClO_4$ (0,4 g) dissolved in 20 ml distilled water was added to the cooled reaction mixture. Good quality micro-crystals of catalyst system $Co_3(O)$ were obtained from the solution kept at 278 K.

EXAMPLE 4

This example illustrates the preparation of the solid catalyst containing the organometallic oxo-bridged Co/Mn cluster complex designated as $CoMn_2(O)$—Y. Mixed metal Co—Mn(II) exchanged zeolite-HY was prepared by ion-exchange method, in which zeolite HY (7 g) was interacted with 4.3 g of manganese acetate tetrahydrate and 1.43 g of cobalt acetate tetrahydrate dissolved in 100 ml distilled water at 333 K with constant stirring. The solid product was then washed thoroughly with water (500 ml) and dried at 373 L CoMn—Y thus prepared was taken in 15 ml glacial acetic acid and to this was added pyridine (3 ml), NaBr (0.5 g) and aq. $H_2O_2$ (50%, 10 ml) and distilled water (5 ml). The reaction mixture was stirred while passing air, for 2 h at 298 K. The purple solid zeolite ($CoMn_2(O)$ cluster complex encapsulated in zeolite-Y; $CoMn_2(O)$—Y) was then filtered, washed with acetic acid and dried at 298 K under vacuum.

EXAMPLE 5

This example illustrates the preparation of solid catalyst containing organometallic oxo-bridged Mn cluster catalyst designated as $Mn_3(O)$—Y. Manganese exchanged zeolite-HY (Mn—Y) was prepared by the ion-exchange method, in which zeolite HY (7 g) was interacted with 4.3 g of manganese acetate tetrahydrate dissolved in 100 ml distilled water at 333 K with constant stirring for 4–5 h. The solid product was then filtered, washed thoroughly with water (500 ml) and dried at 373 K. Mn—Y thus prepared was taken in 15 ml glacial acetic acid and to this was added pyridine (3 ml)), NaBr (0.5 g) and aq. $H_2O_2$ (50%, 10 ml) and distilled water (5 ml). The reaction mixture was stirred while passing air, for 2 h at 298 K. The pale brown solid zeolite ($Mn_3(O)$ cluster complex encapsulated in zeolite-Y; $Mn_3(O)$—Y) was then filtered, washed with acetic acid and dried at 298 K under vacuum.

EXAMPLE 6

This example illustrates the preparation of the solid catalyst containing organometallic oxo-bridged Co cluster catalyst designated as $Co_3(O)$—Y. Cobalt exchanged zeolite-HY (Co—Y) was prepared by the ion-exchange method, in which zeolite HY (7 g) was interacted with 4.3 g of cobalt acetate tetrahydrate dissolved in 100 ml distilled water at 333 K with constant stirring for 4–5 h. The solid product was then filtered, washed thoroughly with water (500 ml) and dried at 373 K. Co—Y thus prepared was taken in 15 ml glacial acetic acid. To this was added pyridine (3 ml), NaBr (0.5 g) and aq. $H_2O_2$ (50%, 10 ml) and distilled water (5 ml). The reaction mixture was stirred while passing air, for 2 h at 298 K. The pink solid zeolite ($Co_3(O)$ cluster complex encapsulated in zeolite-Y; $Co_3(O)$—Y) was then filtered, washed copiously with acetic acid and dried at 298 K under vacuum.

Preparation of Adipic Acid

EXAMPLE 7

This example illustrates the procedure for the preparation of adipic acid from cyclohexanone by using cluster catalyst $Co_3(O)$, $Mn_3(O)$ or $CoMn_2(O)$ at 363 K and 550 psig air pressure. The experiments were conducted in a closed titanium-lined pressure reactor (Parr 4843). In a typical oxidation experiment, 4.21 ml of cyclohexanone was taken in 38 ml of glacial acetic acid and 1.9 ml of distilled water. To it 0.114 ml of methylethylketone (MEK) was added. Then 0.354 g of the cluster catalyst ($CoMn_2(O)$, $Mn_3(O)$ or $Co_3(O)$; prepared as reported in Examples 1–3) was added to the reaction mixture which was then heated to 363 K. This was followed by pressurizing the reactor with air to 550 psig, The reaction was conducted for 4 h. Then, the temperature of the reactor was quenched to 293 K using ice. Conversion of cyclohexanone and liquid products distribution was checked by gas chromatographic analysis (Shimadzu GC 14 B. SE-30 S.S. packed column). Later, 2 ml of the reaction mixture was taken and esterified with 5 ml of $BF_3$ in methanol by refluxing for 8 h. Subsequent treatments of separation yielded the esterified products. These were then dissolved in anhydrous dichloromethane (3 ml) and analyzed by GC (Shimadzu GC 14 B, capillary column).

EXAMPLE 8

This example illustrates the procedure for the preparation of adipic acid from cyclohexanone using $CoMn_2(O)$ cluster catalyst at 353 K. The experiments were conducted in a closed titanium-lined pressure reactor (Parr 4843). In a typical oxidation experiment, 4.21 ml of cyclohexanone was taken in 38 ml of glacial acetic acid and 1.9 ml of distilled water. To it 0.114 ml of methylethylketone (MEK) was added. Then 0.354 g of $CoMn_2(O)$ prepared as reported in Example 1 was added to the reaction mixture which was then heated to 353 K. This was followed by pressurizing the reactor with air to 550 psig. The reaction was conducted for 4 h. Then, the temperature of the reactor was quenched to 293 K using ice. Conversion of cyclohexanone and liquid products distribution was checked by gas chromatographic analysis (Shimadzu GC 14 B, SE-30 S.S. packed column). Later, 2 ml of the reaction mixture was taken and esterified with 5 ml of $BF_3$ in methanol by refluxing for 8 h. Subsequent treatments of separation yielded the esterified products. These were then dissolved in anhydrous dichloromethane (3 ml) and analyzed by GC (Shimadzu GC 14 B, capillary column).

EXAMPLE 9

This example illustrates the procedure for the preparation of adipic acid from cyclohexanone using $CoMn_2(O)$ cluster catalyst at 373 K. The experiments were conducted in a closed titanium-lined pressure reactor (Parr 4843). In a typical oxidation experiment, 4.21 ml of cyclohexanone was taken in 38 ml of glacial acetic acid and 1.9 ml of distilled water. To it 0.114 ml of methylethylketone (MEK) was added. Then 0.354 g of $CoMn_2(O)$ prepared as reported in Example 1 was added to the reaction mixture which was then heated to 373 K. This was followed by pressurizing the reactor with air to 550 psig. The reaction was conducted for 0.75 or 4 h. Then, the temperature of the reactor was quenched to 293 K using ice. Conversion of cyclohexanone and liquid products distribution was checked by gas chromatographic analysis (Shimadzu GC 14 B, SE-30 S.S. packed column). Later, 2 ml of the reaction mixture was taken and esterified with 5 ml of $BF_3$ in methanol by refluxing for 8 h. Subsequent treatments of separation yielded the esterified products. These were then dissolved in anhydrous dichloromethane (3 ml) and analyzed by GC (Shimadzu GC 14 B, capillary column).

EXAMPLE 10

This example illustrates the procedure for the preparation of adipic acid from cyclohexanone at 383 K using $CoMn_2$ (O) cluster catalyst. The experiments were conducted in a closed titanium-lined pressure reactor (Parr 4843). In a typical oxidation experiment, 4.21 ml of cyclohexanone was taken in 38 ml of glacial acetic acid and 1.9 ml of distilled water. To it 0.114 ml of methylethylketone (MEK) was added. Then 0.354 g of $CoMn_2(O)$ prepared as reported in Examples 1 was added to the reaction mixture which was then heated to 383 K. This was followed by pressurizing the reactor with air to 550 psig. The reaction was conducted for 4 h. Then, the temperature of the reactor was quenched to 293 K using ice. Conversion of cyclohexanone and liquid products distribution was checked by gas chromatographic analysis (Shimadzu GC 14 B, SE-30 S.S. packed column). Later, 2 ml of the reaction mixture was taken and esterified with 5 ml of $BF_3$ in methanol by refluxing for 8 h. Subsequent treatments of separation yielded the esterified products. These were then dissolved in anhydrous dichloromethane (3 ml) and analyzed by GC (Shimadzu GC 14 B. capillary column).

The prior-art catalyst, a physical mixture of $Co(CH_3COO)_2.4H_2O$ (0.3106 g) and $Mn(CH_3COO)_2.4H_2O$ (0.0791 g) was used for comparison with MEK or bromide ion as oxidation initiator.

EXAMPLE 11

This example illustrates the procedure for the preparation of adipic acid from cyclohexanone using solid $\mu_3$-oxo-bridged organometallic Co/Mn cluster catalyst $CoMn_2(O)$—Y. The experiments were conducted in a closed titanium-lined pressure reactor (Parr 4843). In a typical oxidation experiment 4.21 ml of cyclohexanone was taken in 38 ml of glacial acetic acid and 1.9 ml of distilled water. To it, 0.114 ml of methylethylketone (MEK) was added. Then 74.9, 149.8, 299.5 or 599.0 mg of $CoMn_2(O)$—Y catalyst prepared as reported in Example 4 was added. The reaction mixture then pressured with air to 700 psig and then heated to 373 K. The reaction was conducted for 4 h. At the end of the reaction, the temperature of the reactor was quenched to 293 K using ice. The solid catalyst was separated from the reaction mixture by filtration and the conversion of cyclohexanone and liquid products, if any, were checked by gas chromatographic analysis (Shimadzu GC 14 B SE-30 S.S. packed column). Later, 2 ml of the reaction mixture was taken and esterified with 5 ml of $BF_3$ in methanol by refluxing for 8 h. Subsequent treatments separation yielded the esterified products. These were then dissolved in anhydrous dichloromethane (3 ml) and analyzed by GC (Shimadzu GC 14 B, capillary column). The solid product containing adipic acid was isolated from the solution by distilling out the acetic acid.

EXAMPLE 12

This example illustrates the procedure for the preparation of adipic acid from cyclohexanone using the solid oxo-bridged organometallic Co/Mn cluster catalyst $CoMn_2(O)$—Y at 500 or 900 psig air pressure. The experiments were conducted in a closed titanium-lined pressure reactor (Parr 4843). In a typical oxidation experiment 4.21 ml of cyclohexanone was taken in 38 ml of glacial acetic acid and 1.9 ml of distilled water. To it, 0.114 ml of methylethylketone (MEK) was added. Then 74.9, 149.8, 299.5 or 599.0 mg of $CoMn_2(O)$—Y catalyst prepared as reported in Example 4 was added, The reaction mixture then pressured with air to 500 or 900 psig and then heated to 373 K. The reaction was conducted for 4 h. At the end of the reaction, the temperature of the reactor was quenched to 293 K using ice. The solid catalyst was separated from the reaction mixture by filtration and the conversion of cyclohexanone and liquid products, if any, were checked by gas chromatographic analysis (Shimadzu GC 14 B SE-30 S.S. packed column). Later, 2 ml of the reaction mixture was taken and esterified with 5 ml of $BF_3$ in methanol by refluxing for 8 h. Subsequent treatments separation yielded the esterified products. These were then dissolved in anhydrous dichloromethane (3 ml) and analyzed by GC (Shimadzu GC 14 B, capillary column). The solid product containing adipic acid was isolated from the solution by distilling out the acetic acid.

EXAMPLE 13

This example illustrates the procedure for the preparation of adipic acid from cyclohexanone using the solid organometallic Mn cluster catalyst $Mn_3(O)$—Y. The experiments were conducted in a closed titanium-lined pressure reactor (Parr 4843). In a typical oxidation experiment 4.21 ml of cyclohexanone was taken in 38 ml of glacial acetic acid and 1.9 ml of distilled water. To it, 0.114 ml of methylethylketone (MEK) was added. Then 299.5 mg of $Mn_3(O)$—Y catalyst prepared as reported in Example 5 was added. The reaction mixture then pressured with air to 700 psig and then heated to 373 K. The reaction was conducted for 4 h. At the end of the reaction, the temperature of the reactor was quenched to 293 K using ice. The solid catalyst was separated from the reaction mixture by filtration and the conversion of cyclohexanone and liquid products, if any, were checked by gas chromatographic analysis (Shimadzu GC 14 B SE-30 S.S. packed column). Later, 2 ml of the reaction mixture was taken and esterified with 5 ml of $BF_3$ in methanol by refluxing for 8 h. Subsequent treatments separation yielded the esterified products, These were then dissolved in anhydrous dichloromethane (3 ml) and analyzed by GC (Shimadzu GC 14 B, capillary column). The solid product containing adipic acid was isolated from the solution by distilling out the acetic acid.

EXAMPLE 14

This example illustrates the procedure for the preparation of adipic acid from cyclohexanone using the solid organometallic Co cluster catalyst $Co_3(O)$—Y. The experiments were conducted in a closed titanium-lined pressure reactor (Parr 4843). In a typical oxidation experiment 4.21 ml of cyclohexanone was taken in 38 ml of glacial acetic acid and 1.9 ml of distilled water. To it, 0.114 ml of methylethylketone (MEK) was added. Then 299.5 mg of $Co_3(O)$—Y catalyst prepared as reported in Example 6 was added. The reaction mixture then pressured with air to 700 psig and then heated to 373 K. The reaction was conducted for 4 h. At the end of the reaction, the temperature of the reactor was quenched to 293 K using ice. The solid catalyst was separated from the reaction mixture by filtration and the conversion of cyclohexanone and liquid products, if any, were checked by gas chromatographic analysis (Shimadzu GC 14 B SE-30 S.S. packed column). Later, 2 ml of the reaction mixture was taken and esterified with S ml of $BF_3$ in methanol by refluxing for 8 h. Subsequent treatments separation yielded the esterified products. These were then dissolved in anhydrous dichloromethane (3 ml) and analyzed by GC (Shimadzu GC 14 B, capillary column). The solid product containing adipic acid was isolated from the solution by distilling out the acetic acid.

EXAMPLE 15

This example illustrates the procedure for the preparation of adipic acid from cyclohexanol using solid $\mu_3$-oxo-bridged organometallic Co/Mn cluster catalyst $CoMn_2(O)$—Y. The experiments were conducted in a closed titanium-lined pressure reactor (Parr 4843). In a typical oxidation experiment 4.3 ml of cyclohexanol was taken in 38 ml of glacial acetic acid and 1.9 ml of distilled water. To it, 0.114 ml of methylethylketone (MEK) was added. Then 74.9 mg of $CoMn_2(O)$—Y catalyst prepared as reported in Example 4 was added. The reaction mixture was then pressured with air to 700 psig and heated to 373 K. The reaction was conducted for 4 h. At the end of the reaction, the temperature of the reactor was quenched to 293 K using ice. The solid catalyst was separated from the reaction mixture by filtration and the conversion of cyclohexanol and liquid products were checked by gas chromatographic analysis (Shimadzu GC 14 B SE-30 S.S, packed column). Later, 2 ml of the reaction mixture was taken out and esterified with 5 ml of $BF_3$ in methanol by refluxing for 8 h. Subsequent treatments yielded the esterified products. These were then dissolved in anhydrous dichloromethane (3 ml) and analyzed by GC (Shimadzu GC 14 B, capillary column). The solid product containing adipic acid was isolated from the solution by distilling out the acetic acid.

EXAMPLE 16

This example illustrates the procedure for the preparation of adipic acid from a mixture of cyclohexanone and cyclohexanol using solid $\mu_3$-oxo-bridged organometallic Co/Mn cluster catalyst $CoMn_2(O)$—Y. The experiments were conducted in a closed titanium-lined pressure reactor (Parr 4843). In a typical oxidation experiment 2.1 ml of cyclohexanone and 2.1 ml of cyclohexanol were taken in 38 ml of glacial acetic acid and 1.9 ml of distilled water. To it, 0.114 ml of methylethylketone (MEK) was added Then 74.9 mg of $CoMn_2(O)$—Y catalyst prepared as reported in Example 4 was added. The reaction mixture then pressured with air to 700 psig and then heated to 373 K. The reaction was conducted for 4 h. At the end of the reaction, the temperature of the reactor was quenched to 293 K using ice. The solid catalyst was separated from the reaction mixture by filtration and the substrate conversion and liquid products. if any, were checked by gas chromatographic analysis (Shimadzu GC 14 B SE-30 S.S. packed column). Later, 2 ml of the reaction mixture was taken and esterified with 5 ml of $BF_3$ in methanol by refluxing for 8 h. Subsequent treatments yielded the esterified products. These were then dissolved in anhydrous dichloromethane (3 ml) and analyzed by GC (Shimadzu GC 14 B, capillary column). The solid product containing adipic acid was isolated from the solution by distilling out the acetic acid.

The catalytic data for the oxidation of cyclohexanone, cyclohexanol and a mixture thereof to adipic acid using $\mu_3$-oxo-bridged Co/Mn cluster complex catalysts are listed in Tables 1, 2 and 3.

TABLE 1

Oxidation of cyclohexanone with air over organometallic oxo-bridged cluster catalysts

| | | | | | Productive selectivity (wt. %) | | |
| --- | --- | --- | --- | --- | --- | --- | --- |
| Catalyst system | Promoter | Temperature (K) | Time (h) | Conv. Wt. % | Succinic acid | Glutaric acid | Adipic acid |
| $Co_3(O)$ | MEK | 363 | 4 | 11.9 | 10.6 | 15.1 | 74.3 |
| $Mn_3(O)$ | MEK | 363 | 4 | 93.7 | 3.0 | 13.9 | 83.1 |
| $CoMn_2(O)$ | MEK | 363 | 4 | 92.2 | 6.9 | 14.7 | 78.4 |
| $CoMn_2(O)$ | MEK | 353 | 4 | 54.4 | 3.1 | 5.7 | 81.2 |
| $CoMn_2(O)$ | MEK | 373 | 0.75 | 66.1 | 3.9 | 15.3 | 80.8 |
| $CoMn_2(O)$ | MEK | 373 | 4 | 97.6 | 1.9 | 11.5 | 86.6 |
| $CoMn_2(O)$ | MEK | 383 | 4 | 56.6 | 24.5 | 16.7 | 58.8 |
| Co + Mn (3:1) | NaBr | 363 | 2 | 89.2 | 9.4 | 16.6 | 74.0 |
| Co + Mn (3:1) | NaBr | 363 | 4 | 94.9 | 6.5 | 14.9 | 78.6 |
| Co + Mn (3:1) | MEK | 363 | 4 | 87.8 | 3.8 | 12.0 | 84.2 |
| Co + Mn (3:1) | NaBr | 363 | 8 | 91.1 | 10.0 | 11.8 | 78.2 |
| Co + Mn (3:1) | MEK | 363 | 8 | 94.7 | 3.6 | 13.1 | 83.3 |

TABLE 2

Oxidation of cyclohexanone to adipic acid with air over solid catalysts contain $\mu_3$-oxo-bridged Co/Mn cluster complexes

| Catalyst system | | Pressure | | Productive selectivity (wt. %) | | | |
| --- | --- | --- | --- | --- | --- | --- | --- |
| (amount of catalyst) | Promoter | (psi) (cold) | Conv. wt. % | Succinic acid | Glutaric acid | Valeric acid | Adipic acid |
| $Co_3(O)$—Y (299.5 mg) | MEK | 700 | 10.2 | 0.9 | 6.6 | | 92.5 |
| $Mn_3(O)$—Y (299.5 mg) | MEK | 700 | 96.8 | 2.8 | 14.1 | 1.6 | 81.5 |
| $CoMn_2(O)$—Y (74.9 mg) | MEK | 700 | 98.3 | 1.8 | 10.9 | — | 87.3 |
| $CoMn_2(O)$—Y (149.8 mg) | MEK | 700 | 98.4 | 3.90 | 15.50 | 1.30 | 79.3 |
| $CoMn_2(O)$—Y (299.5 mg) | MEK | 500 | 95.2 | 1.37 | 10.83 | — | 87.8 |

TABLE 2-continued

Oxidation of cyclohexanone to adipic acid with air over solid catalysts contain $\mu_3$-oxo-bridged Co/Mn cluster complexes

| Catalyst system (amount of catalyst) | Promoter | Pressure (psi) (cold) | Conv. wt. % | Productive selectivity (wt. %) | | | |
|---|---|---|---|---|---|---|---|
| | | | | Succinic acid | Glutaric acid | Valeric acid | Adipic acid |
| CoMn$_2$(O)—Y (299.5 mg) | MEK | 700 | 98.4 | 4.52 | 16.52 | 1.97 | 77.0 |
| CoMn$_2$(O)—Y (299.5 mg) | MEK | 900 | 94.8 | 3.38 | 14.27 | 2.53 | 79.8 |
| CoMn$_2$(O)—Y (599.0 mg) | MEK | 700 | 92.7 | 4.13 | 16.51 | 0.144 | 79.2 |

TABLE 3

Oxidation of cyclohexanone/cyclohexanol to adipic acid over CoMn$_2$(O)—Y catalyst

| Run No. | Substrate | Initiator | Conv (wt. %) | Productive distribution (wt. %) | | | | |
|---|---|---|---|---|---|---|---|---|
| | | | | Cyclohexanone | SA | GA | VA | AA |
| 1 | Cyclohexanone + Cyclohexanol (50:50) | MEK | 89.6 | 0 | 4.3 | 14.1 | 0.2 | 81.4 |
| 2 | Cyclohexanol (100) | MEK | 45.0 | 39.0 | 4.1 | 0 | 0 | 1.9 |

The process described above has the combined unique advantages of high conversion of cyclohexanone accompanied with high selectivity of adipic acid and low concentration of other by-product impurities. The process is environmental-friendly and results in no undesired toxic effluents.

We claim:

1. An improved process for the preparation of adipic acid which comprises oxidizing a cyclic compound selected from the group consisting of cyclohexanol, cyclohexanone and a mixture thereof in a polar solvent with oxygen in the presence of an $\mu_3$-oxo-bridged Co/Mn cluster complex catalyst and an oxidation initiator, at a pressure of at least 130 psig, at a temperature ranging between 353 and 403 K, for a period ranging from 0.5 to 8.0 hrs, bringing the temperature of reaction mixture to an ambient temperature and recovering the adipic acid from the reaction mixture by conventional methods.

2. An improve process as claimed in claim 1 wherein the cluster complex has a general formula

[Co$_x$Mn$_y$(O)(OOCR)$_n$]

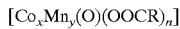

wherein x and y can take values of 0, 1, 2 or 3 and x+y=3, R is selected from the group consisting of alkyl, substituted alkyl group containing 1 or more carbon atoms, aryl and substituted aryl group and n is in the range of 4 to 6.

3. An improved process as claimed in claim 1, wherein the $\mu_3$-oxo cluster complex used is contained in a solid matrix selected from the group consisting of aluminosilicate zeolite, aluminophosphates, carbon molecular sieves and silica.

4. An improved process as claimed in claim 1, wherein the polar solvent used is a mixture of alkyl or aryl carboxylic acid and water.

5. An improved process as claimed in claim 1, wherein the oxygen used is selected from the group consisting of pure oxygen, air and a mixture of inert gases and oxygen.

6. An improved process as claimed in claim 1, wherein the oxidation initiator used is selected from the group consisting of methyl ethyl ketone (MEK), acetaldehyde, hydrogen peroxide, alkyl hydroperoxide and halide ion.

7. An improved process as claimed in claim 2, wherein the $\mu_3$-oxo cluster complex used is contained in a solid matrix selected from the group consisting of aluminosilicate zeolite, aluminophosphates, carbon molecular sieves and silica.

8. An improved process as claimed in claim 2, wherein the polar solvent used is a mixture of alkyl or aryl carboxylic acid and water.

9. An improved process as claimed in claim 3, wherein the polar solvent used is a mixture of alkyl or aryl carboxylic acid and water.

10. An improved process as claimed in claim 7, wherein the polar solvent used is a mixture of alkyl or aryl carboxylic acid and water.

11. An improved process as claimed in claim 2, wherein the oxygen used is selected from the group consisting of pure oxygen, air and a mixture of inert gases and oxygen.

12. An improved process as claimed in claim 3, wherein the oxygen used is selected from the group consisting of pure oxygen, air and a mixture of inert gases and oxygen.

13. An improved process as claimed in claim 7, wherein the oxygen used is selected from the group consisting of pure oxygen, air and a mixture of inert gases and oxygen.

14. An improved process as claimed in claim 4, wherein the oxygen used is selected from the group consisting of pure oxygen, air and a mixture of inert gases and oxygen.

15. An improved process as claimed in claim 8, wherein the oxygen used is selected from the group consisting of pure oxygen, air and a mixture of inert gases and oxygen.

16. An improved process as claimed in claim 9, wherein the oxygen used is selected from the group consisting of pure oxygen, air and a mixture of inert gases and oxygen.

17. An improved process as claimed in claim 10, wherein the oxygen used is selected from the group consisting of pure oxygen, air and a mixture of inert gases and oxygen.

* * * * *